United States Patent [19]
Marnay et al.

[11] Patent Number: 5,658,285
[45] Date of Patent: Aug. 19, 1997

[54] REHABITABLE CONNECTING-SCREW DEVICE FOR A BONE JOINT, INTENDED IN PARTICULAR FOR STABILIZING AT LEAST TWO VERTEBRAE

[75] Inventors: Thierry Marnay, Nimes; Jean Huppert, L'Etrat; Marc Ameil, Reims, all of France

[73] Assignee: JBS S.A., Sainte Savine, France

[21] Appl. No.: 549,123

[22] Filed: Oct. 27, 1995

[30] Foreign Application Priority Data

Oct. 28, 1994 [FR] France .................. 94 13103

[51] Int. Cl.[6] .................................. A61B 17/70
[52] U.S. Cl. .................. 606/61; 606/73; 606/76; 606/69; 411/395
[58] Field of Search ............... 606/60, 61, 72, 606/73, 76, 77; 411/395, 82, 258; 623/17

[56] References Cited

U.S. PATENT DOCUMENTS 5,025,373  6/1991  Keyser, Jr. et al. .
5,108,395  4/1992  Laurain ........................ 606/61

Primary Examiner—Guy V. Tucker
Assistant Examiner—David O. Reip
Attorney, Agent, or Firm—Ostrolenk, Faber, Gerb & Soffen, LLP

[57] ABSTRACT

A screw device for a bone joint particularly for stabilizing at least two vertebrae includes a monobloc tubular body with a thread on its exterior, and being longitudinally grooved on its interior deep enough as to form openings at the root of the thread communicating between the exterior of the body at the root and the interior of the body. The openings in the tubular body having circumferential cutting edges. A closure element is provided for screwed attachment to the open end of the tubular body.

18 Claims, 3 Drawing Sheets

REHABITABLE CONNECTING-SCREW DEVICE FOR A BONE JOINT, INTENDED IN PARTICULAR FOR STABILIZING AT LEAST TWO VERTEBRAE

BACKGROUND OF THE INVENTION

The present invention relates to a rehabitable connecting-screw device for a bone joint intended, in particular, but not exclusively, for stabilizing at least two vertebrae.

In the case of an irreparable injury to a intervertebral disk, it is necessary either to proceed with its ablation and replace it with a prosthesis, or to effect an intervertebral blocking, that is to say, to immobilize one of the two adjacent vertebrae with respect to the other.

Such a blocking is generally effected by means of screwed metal plates. But, intervertebral prostheses are preferably employed, which favor the growth of the bone in the substance between the vertebrae so as to permit their fusion.

For this purpose, a prosthetic implant is used with upper and lower faces which are adapted to anchor themselves in the bodies of the vertebrae to be stabilized. The implant is open to permit the growth and the bone fusion. The solidarity of the implant is possibly supplemented by a threading so as to avoid possible sliding.

This type of implant has drawbacks, due, in particular, to the large number of parts involved, which makes the implanting difficult.

In order to alleviate certain of these drawbacks, U.S. Pat. No. 5,026,373 and EP-A 0 369 603 propose fusion cages which can be implanted in pairs on two opposite sides of the discal space. Each cage consists of a helicoidal wire having turns which are connected by internal longitudinal bars. The cage is screwed into an internally threaded hole formed between the two vertebrae in the bodies of the vertebrae. Bone substance is placed within the cage. The growth of the bone substance permits its fusion with the surrounding bone substance.

This type of cage, however, has drawbacks due, in particular, to the fact that the inner longitudinal bars are secured to the helicoidal wire by welding and because progressive oxidation of the welds is noted despite the different treatments.

In the case of injury to one or more vertebrae, it is advisable to stabilize the spinal column at the level of this injury and then use a plate which sits astride the injured vertebra or vertebrae and is firmly attached by means of screws at its ends to sound vertebrae, as described in FR-A-2 651 992.

The drawback of this type of device resides in the large number of its parts, and furthermore, it requires placing screws in different axes, which complicates the surgical intervention.

Furthermore, fastening by means of screws is not always reliable over the course of time, due to stresses of the spinal column, and one or more screws may become stripped, with serious consequences for the patient.

Another important drawback of these devices is that each of them is intended for one type of intervention and therefore each requires a specific accessory.

SUMMARY OF THE INVENTION

The present invention is directed at remedying the various above drawbacks of known devices by providing a rehabitable connecting screw device for bone joints intended for stabilizing at least two vertebrae. It is adapted to be put in place with a single accessory. It is also capable of being used for bone consolidation and coaptation of two bone fragments.

The connecting screw device of the invention is characterized essentially by the fact that it comprises a monobloc tubular body having a thread on its outside. The root of the thread is provided with openings which debouch into the interior of the tubular body. One of the ends of the tubular body comprises on its inner side a thread which permits the screw attachment of a threaded closure piece.

Thus, in the case of an intervertebral blocking, the device of the invention is screwed between two vertebrae in an orifice which has been previously drilled and tapped. Then bone substance is introduced into the device. Finally, the closure piece is put in place.

In one particular embodiment of the device of the invention, the closure piece comprises, on the side opposite the thread which permits the screwing thereof into the tubular body, a cylindrical extension which is also threaded and which is split diametrically by a groove which permits the placement in the groove of a bar which is held in the groove by means of a nut screwed onto the extension.

This embodiment makes it possible to fasten a screw in accordance with the invention in each of the vertebrae and to connect them by a bar. Each of the screws is then provided with a closure piece of this type.

On the one hand, the vertebrae may be adjacent or may be separated by one or more other vertebrae. Furthermore, a bar may be firmly attached to more than two screws in accordance with the invention, which are screwed into the body of the vertebrae or between two vertebrae.

The tubular body of the device of the invention can be produced by machining a cylinder of biocompatible metal, which is preferably titanium, possibly treated on its surface by sanding or shot blasting, or coated with a plasma of titanium or with hydroxyapatite. It may also be made of plastic or of bioresorbable material.

The closure piece of the device of the invention may be made of a metal such a titanium, or else of plastic or a bioresorbable material.

Placing the device of the invention does not require the use of extensive mechanical means and can advantageously be effected by endoscopy.

Other advantages and features of the invention will become evident from the following description read with reference to the accompanying drawing which shows various non-limitative embodiments thereof.

DESCRIPTION OF THE PREFERRED EMBODIMENTS

Figure 1:
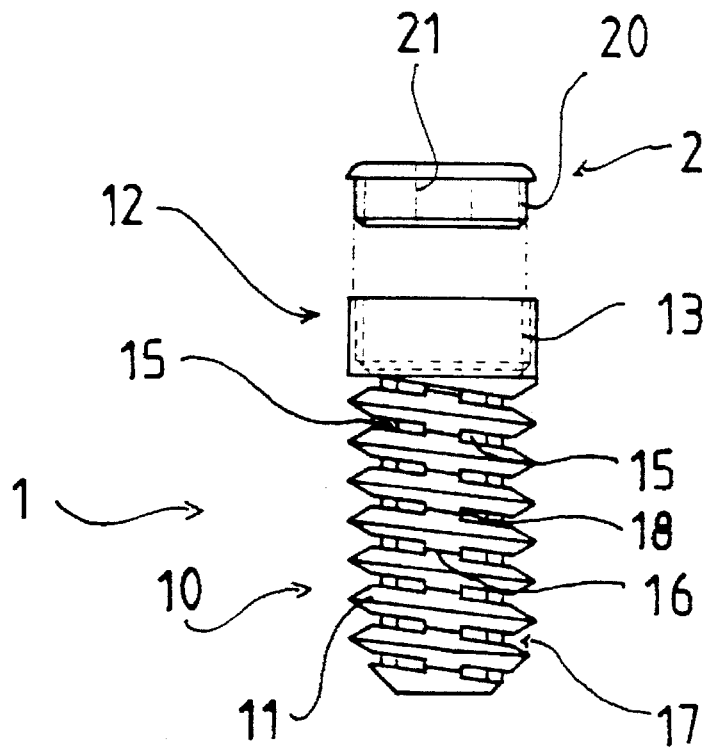
FIG. 1 is a plan view of a first embodiment of a rehabitable screw device in accordance with the invention.
Figure 2:
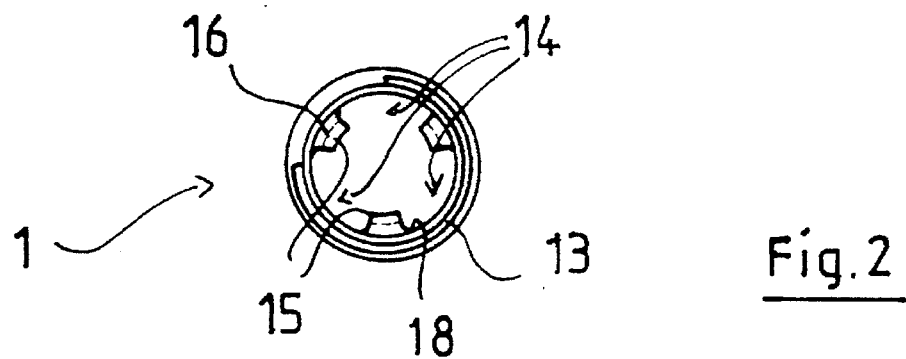
FIG. 2 is a top view of the screw device.

FIGS. 1 and 2 show a rehabitable screw device in accordance with the invention which comprises a tubular body 1 with a lower portion 10 which has a thread 11 on its outer side and with a cup-like upper portion 12 which has a thread 13 inside it.

The internal thread 13 permits the screwing-on of a closure piece 2 which is provided for this purpose with an external thread 20. The piece 2 is intended to close the tubular body 1 after the bone substance has been introduced into it.

The closure piece 2 comprises a hollow cavity 21, for instance of hexagonal shape, which permits its screwing.

The bone substance introduced into the tubular body 1 can be taken from the vertebra or vertebrae upon the production of the tapped hole.

Three grooves 14 are machined longitudinally in the inner wall of the portions 10 and 12 of the tubular body 1, leaving three longitudinal bars 15 of material which are uniformly spaced apart.

The grooves 14 have a radial depth greater than the thickness of the wall of the tubular body at the place of the root 16 of the thread 11. As a result, the thread is cut into, and this creates opposite the grooves 14, between the turns of the thread 11, openings 17 which permit the passage of the bone substance for establishing fusion with the peripheral bone.

The tubular body can be made by different processes, depending on the nature of the material employed. In the case of a biocompatible hard material such as titanium, it will be made by wire machining or by electro-recessing. In the case of a material which is not as hard, such as a plastic or a bioresorbable material, it may be made by injection.

The side edges 18 of the openings 17 in the lower portion 10 are tapered so that upon screwing of the tubular body 1 into the threaded bore tapped in the bone substance, a clipping of the threads of the tapping by the edges 18 takes place, and the removed bone material is introduced into the tubular body 1.

Figure 3:
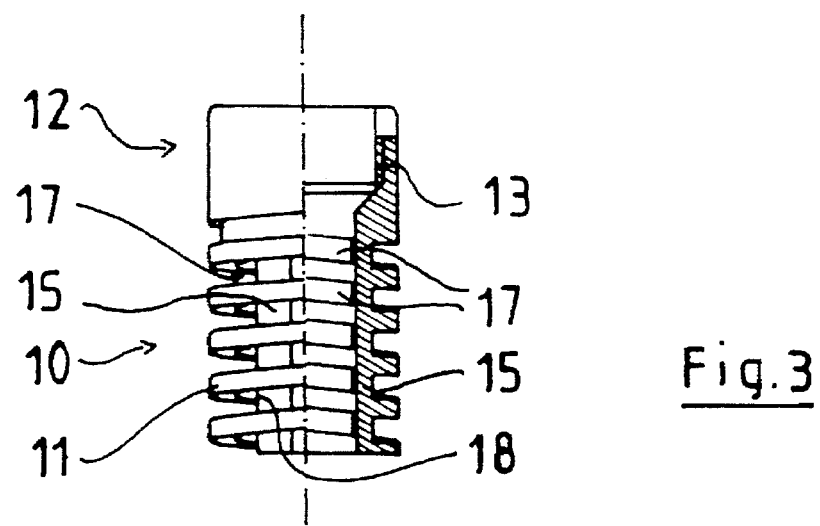
FIG. 3 is a view in longitudinal half-section of a second embodiment of the device in accordance with the invention.

This phenomenon can be amplified by imparting a special profile to the thread 11, such as that shown in FIG. 3. Elements in FIG. 3 that correspond to those in FIG. 1 are identified by the same reference numerals marked with a ' symbol.

In the embodiment of FIG. 3, the profile of the thread 11 is square, and not conical as in the preceding embodiment, so that the side edges 18 of the openings 17 are linear and cutting.

By previously effecting a suitable tapping, the depth of which is greater than that of the thread 11, for instance, there is removed, upon the screwing, a large amount of bone material while effecting a perfect attachment of the tubular body 1.

For the same purpose, the lower end of the thread may have a self tapping notch, in which case no prior tapping is effected, or a shallower tapping is effected, the material removed being also directed toward the inside of the tubular body 1.

Figure 4:
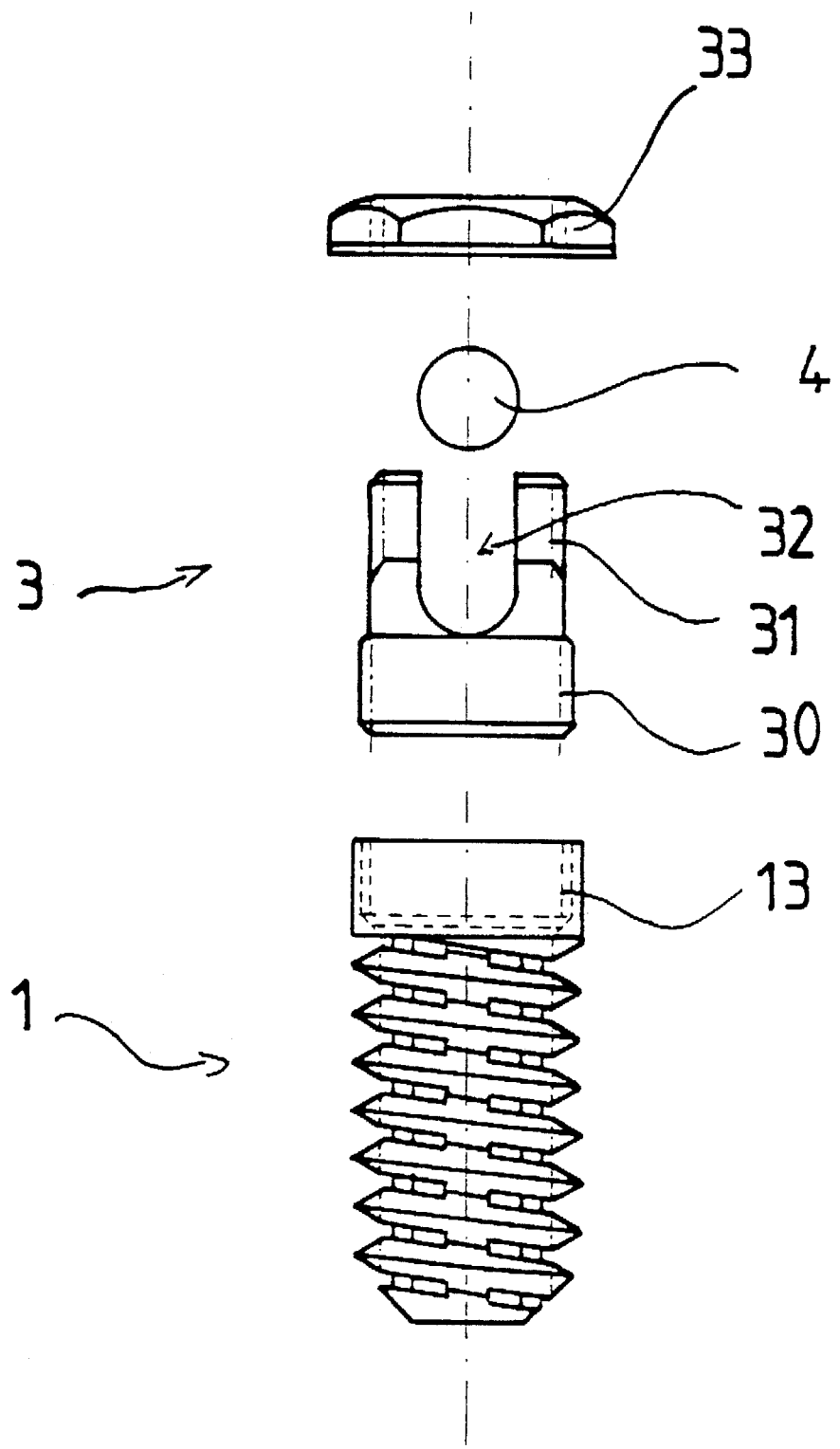
FIG. 4 is a plan view of a variant embodiment of the device in accordance with the invention.

Referring to FIG. 4, in that variant of the device in accordance with the invention, the closure piece 3 comprises, on the side opposite the thread 30, a threaded extension 31 which is split diametrically by a groove 32. That groove permits a bar 4 to be placed in and then locked in the groove 32 by means of a nut 33 which is screwed onto the threaded extension 31.

Figure 5:
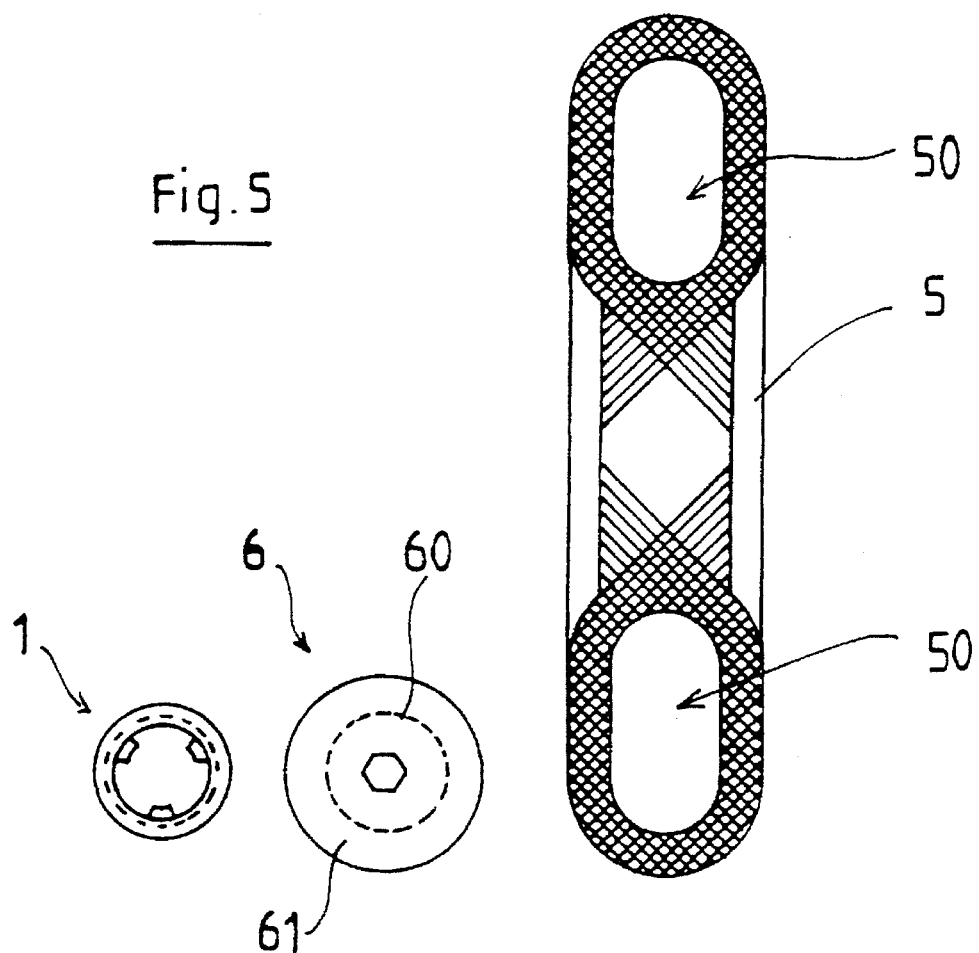
FIGS. 5 and 6 show a top view and a profile view, exploded, of another variant embodiment of the device in accordance with the invention.
Figure 6:
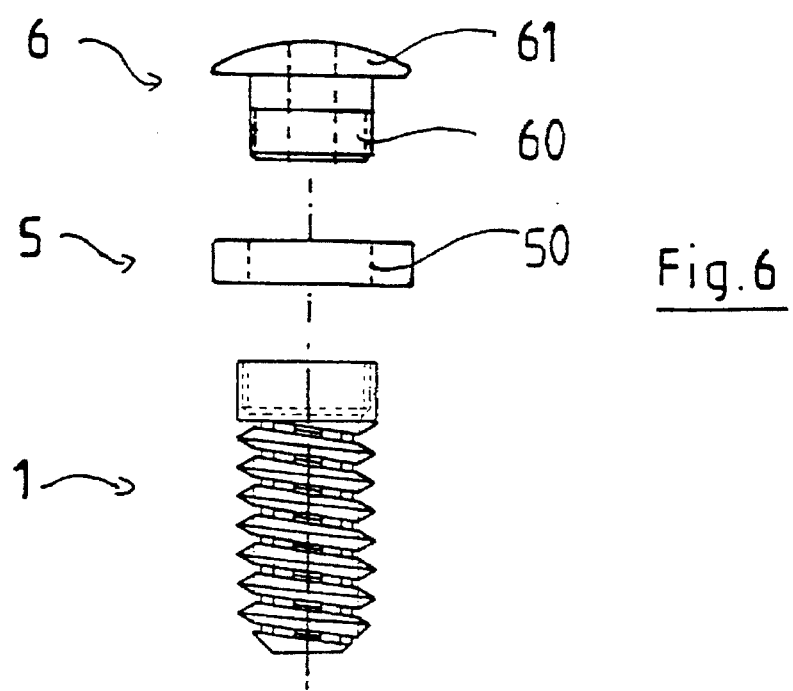

FIGS. 5 and 6 shows another variant of the device of the invention, wherein two screws 1 are connected, although only one screw 1 is shown. The connection can be effected by means of a knurled plate 5 which is pierced at each of its ends by an orifice 50 into which the threaded portion 60 of a closure piece 6 can be introduced and, in order to permit better locking of the plate 5, the threaded portion 60 has a wide flat head 61.

The present invention is not limited to the above description of certain of its embodiments, which may be subjected to various changes without thereby going beyond the scope of the invention.

In particular, it should be pointed out that the tubular body of the device of the invention can be filled with cement before or after it is put in place.

Furthermore, the device in accordance with the invention can be used as an anchoring screw for an osteosynthesis material by mechanical screwing on the female thread of its tubular part of a fastening system with connection on bar, plate or threaded rod.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A rehabitable connecting screw device for a bone joint for stabilizing at least two vertebrae comprising:

a hollow, tubular body having a periphery with a screw thread defined thereon, the screw thread extending radially inward to a root;

the interior of the tubular body having defined in it a plurality of circumferentially spaced apart, longitudinal direction grooves having a radial depth into the interior of the body greater than the thickness of the body at the root of the thread and sufficient to form openings in the body at the root of the thread spaced at intervals around the body and communicating through the openings between the outside of the body and the inside of the body;

the tubular body having opposite ends, including an insertion end and an opposite closable end, and a closure piece attached at the tubular body over the closable end thereof.

2. The screw device of claim 1, wherein the closable end of the tubular body has a female thread therein and the closure piece is threaded for screw attachment to and over the closable end of the tubular body.

3. The device of claim 2, wherein the closure piece has a head on the side thereof away from the threaded part thereof; a plate disposed between the head of the closure piece and the tubular body; the plate having a hole therethrough for the closure piece so that when the closure piece is inserted through the plate, the head of the closure piece is blocked by the plate.

4. The screw device of claim 3 wherein the plate has a plurality of openings therethrough, each for a respective one of the closure pieces.

5. The screw device of claim 1, wherein the tubular body is a monobloc body.

6. The screw device of claim 1, wherein the openings include circumferential side edges and the edges are cutting edges when the screw device is rotated normally in the rotation direction of the screw device for screwing in the screw device.

7. The screw device of claim 1, wherein the openings include circumferential side edges, and at least some of the side edges of the openings are cutting edges.

8. The screw device of claim 7, wherein toward the insertion end of the tubular body, the thread includes a self tapping notch.

9. The screw device of claim 1, wherein on the side of the closure piece away from the tubular body, the closure piece including a threaded cylindrical extension away from the body, and the cylindrical extension including a groove defined therein which splits the cylindrical extension diametrically, wherein the groove is for receiving a bar.

10. In combination, the screw device of claim 9 with a bar disposed in the groove in the cylindrical extension; a nut screwed on the extension for holding the bar in the groove.

11. The device of claim 1, wherein the tubular body is comprised of biocompatible metal.

12. The device of claim 1, wherein the tubular body is surface treated by sanding or shot blasting.

13. The device of claim 1, wherein the tubular body is coated with a plasma of bicompatible metal.

14. The screw device of claim 1, wherein the body is coated with hydroxyapatite.

15. The device of claim 1, wherein the tubular body is comprised of machined titanium.

16. The device of claim 1, wherein the tubular body is comprised of plastic.

17. The device of claim 1, wherein the tubular body is comprised of bioresorbable material.

18. The device of claim 1, wherein the closure piece is comprised of a material selected from the group consisting of biocompatible metal, plastic and bioresorbable material.

* * * * *